US008759051B2

(12) United States Patent
Solomon et al.

(10) Patent No.: US 8,759,051 B2
(45) Date of Patent: *Jun. 24, 2014

(54) CONTROL OF CONTAMINANT MICROORGANISMS IN FERMENTATION PROCESSES WITH PEROXYGEN-RELEASING COMPOUNDS

(75) Inventors: Ethan Baruch Solomon, Wilmington, DE (US); Derrick Otieno Okull, Pleasanton, CA (US); Thomas Peter Tufano, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/329,612

(22) Filed: Dec. 19, 2011

(65) Prior Publication Data

US 2012/0329118 A1 Dec. 27, 2012

Related U.S. Application Data

(60) Provisional application No. 61/425,049, filed on Dec. 20, 2010.

(51) Int. Cl.
*C12P 7/06* (2006.01)
(52) U.S. Cl.
USPC .......................................................... 435/161
(58) Field of Classification Search
USPC .................................................. 435/161, 165
See application file for complete search history.

(56) References Cited

U.S. PATENT DOCUMENTS

| 3,041,250 | A | * | 6/1962 | Wolnak et al. | ................... | 435/43 |
|---|---|---|---|---|---|---|
| 5,264,018 | A | | 11/1993 | Koenigsberg et al. | | |
| 6,045,708 | A | | 4/2000 | Eriksson | | |
| 6,969,487 | B1 | | 11/2005 | Sias et al. | | |
| 7,422,759 | B2 | | 9/2008 | Kepner et al. | | |
| 2006/0289354 | A1 | | 12/2006 | Bryant et al. | | |
| 2010/0291649 | A1 | * | 11/2010 | Solomon et al. | ............... | 435/161 |
| 2011/0117619 | A1 | * | 5/2011 | Hansen et al. | ................. | 435/167 |
| 2012/0322124 | A1 | * | 12/2012 | Okull et al. | .................... | 435/165 |
| 2012/0322125 | A1 | * | 12/2012 | Okull et al. | .................... | 435/165 |
| 2012/0329117 | A1 | | 12/2012 | Solomon et al. | | |
| 2013/0224814 | A1 | * | 8/2013 | Semenza et al. | .............. | 435/161 |

FOREIGN PATENT DOCUMENTS

| CA | 2300807 | A1 | | 3/2000 |
|---|---|---|---|---|
| CA | 2300807 | | * | 9/2000 |
| CN | 1524806 | A | | 2/2003 |
| EP | 0173450 | A2 | | 5/2004 |
| JP | 2004010564 | A | | 1/2004 |
| KR | 845424 | B1 | | 8/2007 |
| KR | 2007081257 | A | | 8/2007 |
| KR | 2009096306 | A | | 9/2009 |
| WO | 2005063043 | A1 | | 7/2005 |
| WO | 2007149450 | A2 | | 12/2007 |
| WO | 2011006019 | A2 | | 1/2011 |
| WO | 2011116042 | A2 | | 9/2011 |
| WO | 2012027469 | A2 | | 3/2012 |

OTHER PUBLICATIONS

Zhu, et al. Bioresource Technology (2010) vol. 101 (13), pp. 4992-5002.
Demain, J. Ind. Microbiol. Biotechnol. (2009) vol. 36(3), pp. 319-332.
Amorim, et al, Sugar can juice and molasses, beet molasses and sweet sorghum: Composition and usage, "The Alcohol Textbook" (2009), Nottingham University Press, Nottingham, pp. 39-46.
Sugarcane Processing, EPA Food and Agricultural Industries Handbook, chapters 9.10.1.1 (sugar cane) available at http://www.epa.gov/ttnchie1/ap42/ch09/ (accessed Dec. 18, 2011).
Bothast, et al, Applied Microbiology and Biotechnology ( 2005), vol. 67(1), pp. 19-25.
Bellissimi, et al., Process Biochemistry (2005), vol. 40(6), pp. 2205-2213.
Knauf, et al., Sugar Industry (2006), vol. 131, pp. 753-758.
Fernandes, et al., Journal of Radioanalytical and Nuclear Chemistry (1998) vol. 234 (1-2), pp. 113-119.
Jacques, Lyons, T.P., Kelsall, D.R, "The Alcohol Textbook", 2003, 423-424, Nottingham University Press, UK.
Basso, et al., FEMS Yeast Res. (2008) vol. , pp. 1155-1163.
Ulllmann's Encyclopedia of Industrial Chemistry, Wiley Online Library, http://onlinelibrary.wiley.com/doi/10.1002/14356007.a06_483.pub2/pdf, accessed Sep. 30, 2010.
Najjar, et al., Letters in Applied Microbiology, vol. 45 (2007) 13-18.
Butzen, Dry-grind Ethanol Production from Corn, Crop Insights, 2008, vol. 18, No. 11, pp. 1-4.
EPA Food and Agricultural Industries Handbook, chapter 9.10.1.2 (sugar beets), available at http://www.epa.gov/ttnchie1/ap42/ch09/ (accessed Dec. 18, 2011).
Fish, et al, Watermelon juice: a promising feedstock supplement, diluent, and nitrogen supplement for ethanol biofuel production, Biotechnology for Biofuels, Aug. 26, 2009, pp. 1-9.
Zheng, et al, Evaluation of Different Biomass Materials as Feedstock for Fermentable Sugar Production, Applied Biochemistry and Biotechnology, 2007, vol. 136-140, pp. 423-435.
Vigo et al., Affinity and durability of magnesium peroxide-based antibacterial agents to cellulosic substrates, Textile Chemist and Colorist, 1999, 31(1), 29-33, American Association of Textile Chemists and Colorists.
Asghari et al., Inactivation of bacteria by solids coated with magnesium peroxide, Journal of Environmental Science and Health, Part A, 1993, A28(4), 779-93, Abstract.
Shiragami et al., Inhibitory effect of calcium peroxide on the growth of *Clostridium*, anaerobic soil bacteria, Nippon Noyaku Gakkaishi, 1991, 16(4), 677-8, Abstract.

(Continued)

*Primary Examiner* — Ralph Gitomer

(57) ABSTRACT

A method for controlling growth of contaminant microorganisms in a fermentation process using a nitrogen-free peroxygen-releasing compound. The method comprises adding the nitrogen-free peroxygen-releasing compound to one or more steps of a fermentation process. In this method, the a nitrogen-free peroxygen-releasing compound may be added to one or more components of a fermentation broth comprising inoculant, fermentable sugar and process water.

23 Claims, No Drawings

(56) References Cited

OTHER PUBLICATIONS

Croner, Sterilization of Mineral water and other beverages by Magnesium Peroxide, Zeitschrift fuer Hygiene und Unfektionskrankheiten, 1909, 58, 487-98, Abstract.

Anon, Magnesium peroxide and its use in the production of bacteria-free and oxygenated mineral water, Mineralwasser-Fabrik, 1908, 23, 198, Abstract.

Freyssinge et al., Purification and sterilisation of drinking water by means of calcium peroxide, Journal Chemical Society, 1905, 18, 49-51, Abstract.

Von Foregger, Alkaline earths and their peroxides, characteristics and applications, Journal fo the Society of Chemical Industry, 1906, 25, 298-302, Abstract.

US EPA Emission Factor and Inventory Group Final Report, Emission Factor Documentation for AP-42, Sugarcane Processing, 9.10.1.1, 1997.

US EPA Emission Factor and Inventory Group Final Report, Emission Factor Documentation for AP-42, Sugarbeet Processing, 9.10.1.2, 1997.

* cited by examiner

CONTROL OF CONTAMINANT MICROORGANISMS IN FERMENTATION PROCESSES WITH PEROXYGEN-RELEASING COMPOUNDS

CROSS REFERENCE(S) TO RELATED APPLICATION(S)

This application claims the priority benefit of U.S. Provisional Patent Application No. 61/425,049, filed Dec. 20, 2010.

FIELD OF THE INVENTION

The present invention relates to a method for controlling microorganism contamination in fermentation processes. This method is of particular use in the production of potable or fuel-grade ethanol.

BACKGROUND OF THE INVENTION

In the last decade, the use of ethanol as a transportation fuel has increased significantly. Ethanol production in the United States rose from approximately 6.4 billion liters in the year 2000 to over 37 billion liters in 2009. The number of ethanol plants increased from 54 in 2000 to 170 in 2009. Similar increases in production and plant construction have occurred in Latin America and Europe. In 2007, the United States Congress enacted the Energy Independence and Security Act (H.R. 6), which set the renewable fuel standard at 136 billion liters of ethanol by the year 2022. If this standard is to be met, the ethanol industry will continue to grow.

Currently both industrial ethanol (e.g., fuel) and beverage ethanol are produced on large scale from agricultural (natural) feedstocks by fermentation processes in which sugar is converted to ethanol and carbon dioxide by inoculant yeast. Many feedstocks can be used to provide the sugar for fermenting, including potentially, any starch or cellulosic material, which includes nearly all plants, as any starch or cellulose can be a precursor to sugar. Some of the common feedstocks particularly suitable for producing fuel ethanol include corn, milo, sorghum, sugar cane, sugar beets and molasses.

The feedstocks used for ethanol production are natural products therefore, a wide variety of microorganisms such as bacteria, fungi, and yeasts are likely to be naturally present in the feedstocks. Commercial fermentation process conditions are not completely sterile, hence these "contaminant microorganisms" will be present in the process. In commercial ethanol production, microorganisms of greatest concern are lactic acid-producing bacteria and acetic acid-producing bacteria. Such bacteria enter the process from several sources including raw materials, equipment, process water, air, and inoculant yeast, among others. Concentrations of such bacteria may increase in the process environment either through introduction with incoming materials (raw materials, water, air, yeast) or naturally proliferate as a result of conditions favorable to bacterial growth. The optimum atmosphere for yeast production is also extremely conducive to the growth of these bacteria. Organic acids produced by the bacteria inhibit the growth of yeasts and thus reduce ethanol production rate. The bacteria may also consume sugars and other nutrients intended for use by the yeast to produce desired products, rendering the entire process less economical.

Many fermentation processes use antibiotics as antimicrobial compositions. Such use has become disfavored due to suspected development of antibiotic-resistant bacteria and accumulation of antibiotic residues in fermentation byproducts. Antibiotic-resistant bacteria are a significant concern in human health.

Byproducts of ethanol production include solids that are collected after distillation of the ethanol product. Such solids include distillers dried grains with solubles (DDGS) and distiller's wet grains with solubles (DWGS). Many countries are considering regulatory actions that would limit or eliminate the use of antibiotics for ethanol production. DDGS and DWGS are sold as animal feed products.

The need for antimicrobial treatments is increasing, not only because of the growth in production volume of ethanol but also the expansion in size of ethanol production facilities. Whereas a plant producing 150-200 million liters per year (MMly) was considered a large facility just a few years ago, 380 MMly (or more) facilities are today's industry standard. In fed-batch processes, the volume of individual fermentation batches has increased significantly. To accommodate this added capacity, the flow rate of feedstock (commonly known as "mash" once it has been prepared for entry into fermentation) into a fermentation system has increased from approximately 2000-3000 liters per minute to 4500-6000 liters per minute in the largest ethanol production facilities.

WO 2007/149450 describes the use of stabilized chlorine dioxide (SCD) to prevent bacterial contamination in ethanol production. SCD is added prior to the onset of significant bacterial growth in ethanol production, as a preventive rather than as a remedial measure. The growth of contaminant bacteria prior to and during the fermentation of sugar to alcohol is thus substantially prevented, creating conditions that enhance growth of inoculant yeast and enable inoculant yeast to produce ethanol without inhibition by organic acids produced by the bacteria.

Patent application CA 2,300,807 describes the use of urea hydrogen peroxide (UHP) to prevent bacterial growth in fermentation processes. UHP is available commercially in only limited quantities as this adduct has production and storage issues. UHP is added to the process prior to the introduction of yeast, thus eliminating a substantial population of bacterial contaminants, and allowing inoculant yeast to convert fermentation feedstocks into ethanol unhindered. UHP can only be utilized prior to the introduction of inoculant yeast, as the yeast is capable of metabolizing, and thus neutralizing the UHP and rendering it inactive against bacteria. UHP is also not stable during storage conditions commonly encountered in the ethanol industry.

Although some methods are known, there remains demand for improved methods, for addressing contaminant microorganisms in the fermentation industry, both for carbohydrate-containing feedstocks and in fermentation processes. An improved method should preferably be antibiotic-free and not result in residues that accumulate in fermentation coproducts or give rise to antibiotic-resistant bacteria. The method should be efficacious at a wide variety of pH ranges and conditions encountered in the fermentation industry. The method should also use treatment that has a reasonable shelf life, prior to use. There is also a need to improve economics of today's larger volume fermentation processes. The present invention meets these needs.

SUMMARY OF THE INVENTION

The present invention provides a method for controlling growth of contaminant microorganisms in a fermentation process using a nitrogen-free peroxygen-releasing compound, such as sodium percarbonate, calcium peroxide, or magnesium peroxide. The method comprises adding a nitrogen-free peroxygen-releasing compound to one or more steps of a fermentation process, wherein the fermentation process comprises (i) providing an inoculant, a fermentable sugar and process water; (ii) introducing separately, or in any combination, the inoculant, fermentable sugar and process water into a fermentation vessel to provide a fermentation broth; (iii) contacting the inoculant with the fermentable sugar in the fermentation vessel at a temperature at which the inoculant converts the fermentable sugar to ethanol. Optionally nutrients are added to one or more of the inoculant, fermentable sugar and process water. Nutrients may also be added directly to the fermentation vessel. The peroxygen-releasing compound may be added to the inoculant, fermentable sugar or process water prior to introducing each of these to the fermentation vessel. Alternatively the peroxygen-releasing compound may be added directly to the fermentation vessel.

The peroxygen-releasing compound may be formulated with nutrients and other products that might prove beneficial to the overall operation of a fermentation process. Nutrients may be used such as urea or diammonium phosphate (to provide a nitrogen source for the inoculant yeast) or minerals such as zinc or magnesium.

The present invention provides a method for controlling the growth of contaminant microorganisms in the reactants (defined hereinbelow) in the fermentation broth, and in the products of a fermentation process. The method also controls growth of contaminant microorganisms on surfaces of components of a fermentation system. The method consists of, consists essentially of, or comprises the step of adding a nitrogen-free peroxygen-releasing compound to a reactant or the fermentation broth, or to a surface or into a vessel of the fermentation system.

The present invention also provides a method that can be used in cleaning-in-place (CIP) applications to treat surfaces of equipment used in fermentation processes. By "CIP" is meant herein that surfaces can be cleaned without the need to disassemble the equipment.

The method includes adding a nitrogen-free peroxygen-releasing compound in an amount effective to control the growth of contaminant microorganisms without detrimental effect on the inoculant used in the fermentation process. The effective amount varies, but can be determined by one skilled in the art in view of the disclosures herein. The peroxygen-releasing compound may be added at a range of concentrations, but is typically added in an amount ranging from 0.0001% to 5% based on the total weight of the fermentation broth.

The method of the present invention further provides a method to control growth of at least one contaminant microorganism in a carbohydrate feedstock wherein the step of providing a fermentable sugar comprises providing a carbohydrate feedstock and contacting the feedstock with a nitrogen-free peroxygen-releasing compound, wherein the carbohydrate content of the feedstock is at least 1% and preferably 1 to 70%, by weight, based on the total feedstock weight wherein the peroxygen-releasing compound is added in an effective amount. Typically the nitrogen-free peroxygen-releasing compound is added in an amount of 0.0001 to 5% of the peroxygen-releasing compound, based on the total weight of the feedstock.

DETAILED DESCRIPTION OF THE INVENTION

The present invention provides methods for controlling the growth of a contaminant microorganism comprising, consisting essentially of, or consisting of, adding a nitrogen-free peroxygen-releasing compound to one or more steps of a fermentation process. Peroxygen-releasing compounds such as sodium percarbonate are added to the process in an amount effective to control growth of contaminant microorganisms without inhibiting the ability of inoculant yeast to convert fermentable sugars into ethanol and carbon dioxide. The peroxygen-releasing compounds may be added at an amount of 0.0001% to 5%, based on the total weight of a fermentation broth comprising an inoculant, fermentable sugar and process water.

The present invention further provides in the step of providing a fermentable sugar, a method to control growth of at least one contaminant microorganism in a carbohydrate feedstock comprising, consisting essentially of, or consisting of, providing a carbohydrate feedstock and adding a nitrogen-free peroxygen-releasing compound to the feedstock.

Definitions

The following terms have the definitions as provided below for use herein.

Aqueous medium means the medium is substantially water, such as for example greater than 80% water, preferably greater than 90% water, more preferably greater than 95% water. The aqueous medium can be greater than 99% water. Process water is an example of an aqueous medium.

Carbohydrate feedstock means a feed used in preparation of or directly as a fermentable sugar. That is, a carbohydrate feedstock is a fermentable sugar or a composition comprising a fermentable sugar or a composition that can be converted to a fermentable sugar.

The carbohydrate feedstock may comprise up to 100% by weight of carbohydrates. Generally the carbohydrate feedstock comprises between 1% and 70% carbohydrate based on the total weight of the feedstock, preferably between 2 and 40%, as a solution or suspension in an aqueous medium. The amount and composition of the carbohydrates in the feedstock can vary depending on the intended end use. For example, corn steep liquor, which is a carbohydrate solution obtained from a wet mill process, may comprise 16.5% carbohydrates. In a wet mill process, corn is soaked or steeped and then separated into various components. The corn steep liquor is the aqueous liquid obtained after the corn has been soaked for an extended period, during which readily fermentable soluble components are extracted from the corn solids into the steep water. The starch component from the wet mill process may comprise up to 40% by weight carbohydrates.

The carbohydrate feedstock may comprise other components generally functioning as adjuncts to the solutions and/or suspensions. For example, the carbohydrate feedstock may comprise enzymes, surfactants, dispersants, antifoaming compositions, minerals, trace elements, and combinations of two or more thereof. These components and other components that act as adjuncts are well-known to those skilled in the art.

Control as applied to growth of a microorganism herein means to reduce and/or prevent the growth of a targeted undesirable contaminant microorganism. Controlling the growth of a microorganism as used herein also includes to maintain the microorganism population at a desired level, to reduce the population of the microorganism to a desired level (partially reduce or even reduce to undetectable limits, e.g., zero population), and/or to inhibit growth of the microorganism.

An effective amount refers herein to an amount of nitrogen-free peroxygen compound that, when added to a fermentation process, is effective to control the growth of contaminant microorganisms without detrimental effect on the inoculant used in the fermentation process.

A fermentable sugar is a reactant and common nutrient for inoculants used in ethanol fermentation processes. The fermentable sugar is a sugar (e.g. glucose) or starch that is converted by action of yeast to ethanol and carbon dioxide. Equation (1) illustrates the process for glucose ($C_6H_{12}O_6$).

$$C_6H_{12}O_6 \rightarrow 2C_2H_5OH + 2CO_2 \qquad (1)$$

A fermentable sugar as used herein is a carbohydrate that is derived from essentially any plant source comprising sugar, starch and/or cellulose, generally provided in the form of a solution or suspension of the sugar, starch and/or cellulose in water. Starch and/or cellulose can be converted by processes known in the art, e.g., using enzymes, to a fermentable sugar for use in the method of this invention. The fermentable sugar can be derived from sources of starch or one or more cellulosic material such as corn, sorghum, wheat, wood chips, milo, barley, millet, sugar cane, sugar beets, molasses, whey, potatoes, wheat straw, corn stover, switch grass, algae, seaweed, and/or other biological sources. The fermentable sugar may also be derived from fruit juice (e.g., grapes, apples). The fermentable sugar may alternatively be derived from non-traditional feedstocks such as wood waste, bagasse, paper waste, and municipal solid waste. Processes are known to those skilled in the art to convert these sources to fermentable sugar. For reference, see, J. Y. Zhu, et al. Bioresource Technology (2010) vol. 101 (13), pp. 4992-5002; and A. L. Demain, J. Ind. Microbiol. Biotechnol. (2009) vol. 36-(3), pp. 319-332.

Conveniently, the fermentable sugar is derived from corn, using either the dry grind or wet mill process. In a dry grind process, corn is ground into meal and processed without separation into its constituent components comprising essentially fiber, starch, oil, and protein. In a wet mill process, corn is soaked or steeped in water and then mechanically separated into its constituent components. The corn starch component from the wet mill process or meal (corn flour) from the dry grind process is mixed with water and enzymes and cooked to solubilize the starch.

Corn starch is a polysaccharide, that is, a polymer made of individual units of glucose. The corn starch is converted to smaller (shorter) polysaccharides, i.e., dextrins, by enzymes (α-amylase). The smaller polysaccharides are converted to glucose (monosaccharide) using the enzyme glucoamylase, thus forming the fermentable sugar.

As an alternative to corn, the fermentable sugar can be derived from molasses. Molasses can be obtained from a variety of sources including sugar cane or sugar beets, for example, as a byproduct of the process to manufacture crystalline sugar. Molasses is typically obtained as a syrup, to which other ingredients may be added in preparation for fermentation. These other ingredients include sugarcane juice, beet juice, water, and vitamins or other nutrients. Whether one or more of the other ingredients are added and the amount added will vary in a molasses-derived fermentable sugar.

As an alternative to corn, the fermentable sugar can be derived from sugar cane juice. Sugar cane juice is juice extracted with water from sugar cane. The extraction of juice from sugarcane is also accomplished by physical crushing, diffusion in water, or other methods generally well known to those skilled in the art. See, for example, H. V. Amorim, et al, in "The Alcohol Textbook" (2009), Nottingham University Press, Nottingham, pp. 39-46; and EPA Food and Agricultural Industries Handbook, chapters 9.10.1.1 (sugar cane) and 0.10.1.2 (sugar beets), available at http://www.epa.gov/tt-nchie1/ap42/ch09/ (accessed Dec. 18, 2011). Sugar cane juice can be used without further processing and added directly to a fermentation vessel as the fermentable sugar.

For purposes herein, steps used to produce carbohydrate feedstocks and fermentable sugars are steps of the fermentation process. That is, the fermentation process comprises steps to produce carbohydrate feedstocks, and steps to convert starch and/or cellulose to a fermentable sugar.

In the fermentation process, carbohydrates, including sugars and starches, is typically present in the fermentation broth at a concentration of about 5 to about 40% (weight/volume), preferably in the range of about 10 to 35% (weight/volume), based on the total volume of the fermentation broth.

Fermentation broth as used herein means the contents of a fermentation vessel during the fermentation process after all reactants have been added and typically comprises fermentable sugar, inoculant, optional nutrients and process water.

Fermentation process as used herein means a process comprising contacting an inoculant, such as yeast, with a fermentable sugar, and optional nutrients, in process water to produce ethanol. A fermentation process can be batch or continuous. In addition, for purposes herein, fermentation also includes steps for preparing or pretreating one or more of the reactants, such as processes to prepare the fermentable sugar from natural sources, and yeast propagation.

The contacting step is performed at a temperature at which the inoculant converts sugar to ethanol and carbon dioxide.

When ethanol is produced via a dry grind process using corn as a feedstock, the fermentation process may comprise one or more of the steps of slurrying of the corn, liquefaction, saccharification, preparing inoculant yeast (propagation), fermenting the mash (actual step of action of inoculant on sugar to produce ethanol), separating and recovering the resultant ethanol, and optionally recycling the spent inoculant yeast. The fermentation process may comprise one or more of the steps of preparing inoculant yeast, preparing the juice by dilution, pasteurization, or other such process, fermenting, separating and recovering the ethanol, and optionally recycling the yeast. It will be understood by those skilled in the art that these process steps may vary, depending on feedstock availability and plant design and plant location.

Fermentation system as used herein comprises components (equipment), such as vessels and pipes in which and through which one or more of the reactants and products of a fermentation process resides or passes. Such equipment have surfaces on which bacteria and other contaminant (undesirable) microorganisms may be present. As part of a fermentation system is a fermentation vessel—the vessel in which the fermentation step of reacting a fermentable sugar with inoculant to produce ethanol occurs.

When ethanol is produced via a dry grind process, the fermentation system may comprise one or more vessels such as a slurry tank, liquefaction tank, saccharification tank, yeast propagation tank, and fermentation vessel. Such vessels and their use are known to those skilled in the art. See, for example, R. J. Bothast and M. A. Schlicher, Applied Microbiology and Biotechnology (2005), vol. 67(1), pp. 19-25. When ethanol is produced via a wet mill process, the fermentation system may comprise one or more vessels such as a steep tank, a separation tank, yeast propagation tank, and fermentation vessel. It will be understood by those skilled in the art that these process steps may vary, depending on feedstock availability and plant design and plant location.

An inoculant is any microorganism added purposely to a process in order to convert a feedstock (input) to a desired product (output). For purposes herein, an inoculant is a microorganism which is capable of converting a fermentable sugar to ethanol. Yeasts are common inoculants used in ethanol fermentation. Yeasts are microorganisms capable of living and growing in either aerobic (with oxygen) or anaerobic (lacking oxygen) environments. An inoculant may also be selected from the group consisting of fungi, and algae that are capable of converting a fermentable sugar to ethanol. For example, ethanol can be produced from cellulose using ethanol-producing bacteria as the inoculant. When used in accordance with the method of this invention, the inoculant bacteria is not adversely affected by the stabilized chlorine dioxide and peroxide compound as are lactic acid- and acetic acid-producing bacteria.

The following discussion is directed to a process in which the inoculant is yeast.

For purposes herein, an inoculant yeast is a yeast which has been deliberately selected for a particular conversion in a reaction system. For example, an inoculant yeast may be selected for production of additional yeast in yeast propagation (such as for use as baker's yeast); an inoculant yeast may be selected for metabolism of a particular nutrient for production of enzymes. In this specific application, an inoculant yeast is selected for fermentation of a fermentable sugar to produce ethanol of desired quality and in desired quantity. Inoculant yeasts are generally selected because of their ability to completely ferment available sugars, tolerance to high levels of osmotic stress, elevated temperatures, and high concentrations of ethanol. Yeast are commonly used in ethanol fermentation. Yeast are microorganisms capable of living and growing in either aerobic (with oxygen) or anaerobic (lacking oxygen) environments. Suitable inoculant yeasts for use in the process of this invention include, but are not limited to *Saccharomyces cerevisiae* (*S. cerevisiae*), *Saccharomyces uvarum* (*S. uvarum*), *Schizosaccharomyces pombe* (*S. pombe*), and *Kluyveromyces* sp.

The inoculant yeast may be introduced into the fermentation vessel as a yeast inoculum, which is an activated form of the inoculant yeast. That is, prior to introducing inoculant yeast into a fermentation vessel, a yeast inoculum is produced by contacting a yeast starter culture and a nutrient composition in a propagation tank to propagate (increase the quantity of) the yeast. The nutrient composition comprises one or more fermentable sugar, enzyme, additional nutrients, and water to grow or activate the yeast. The propagation tank is a separate vessel from the fermentation vessel and is operated at suitable conditions of temperature (e.g., 68-104° F., 20-40° C.). Each inoculant will have preferred temperature for propagation. For example, a temperature of 30-32° C. (86-90° F.) may be particularly suitable for propagating *S. cerevisiae*. While it is recognized that yeast propagation can occur in the fermentation vessel during the fermentation process, activation of yeast in a propagation tank provides a highly active inoculant yeast. Thus, highly active yeast is introduced to the fermentation vessel. Such yeast propagation techniques are known to those skilled in the art. See, for example, E. Bellissimi, et al., Process Biochemistry (2005), vol. 40(6), pp. 2205-2213; and M. Knauf, et al., Sugar Industry (2006), vol. 131, pp. 753-758.

For continuous fermentation processes, there is often no separate yeast propagation tank. Yeast may or may not be recycled in a continuous process. When no recycle is available, yeasts grow and produce ethanol continuously in a stage called a primary fermentation. When recycle is available, such as is common when molasses or sugarcane juice is used as a feedstock for the fermentable sugar, yeasts are recycled by separation from the other fermentation components, (usually using centrifugation) and typically treated with acid in a separate tank (generally called a yeast recycle tank) to condition the yeast cells for a new fermentation cycle. Alternatively, the yeast may be separated from the fermentation broth, then dried and sold as a co-product. These steps are well known to those skilled in the art. See, for example, E. A. N. Fernandes, et al., Journal of Radioanalytical and Nuclear Chemistry (1998) vol. 234 (1-2), pp. 113-119; and L. C. Basso, et al., FEMS Yeast Res. (2008) vol., pp. 1155-1163.

Relative to bacteria, yeasts may have moderate to slow fermentation rates. To compensate for their metabolic rate, large amounts of yeast may be required in large scale industrial ethanol production. Inoculant yeast is generally added to the fermentation process in an amount typically about $1 \times 10^5$ to $1 \times 10^7$ cells per gram of fermentation broth. It will be recognized by those skilled in the art that this amount may vary depending on the method of fermentation employed.

Mash is used herein to refer to a composition comprising a fermentable sugar. Mash includes any mixture of mixed grain or other fermentable carbohydrates in water used in the production of ethanol at any stage from mixing of a fermentable sugar with water to prior to any cooking and saccharification through to completion of fermentation, as defined in Jacques, K. A., Lyons, T. P., Kelsall, D. R, "The Alcohol Textbook", 2003, 423-424, Nottingham University Press, UK.

Microorganisms in the context of this invention are in two categories, desirable and contaminant (undesirable) microorganisms. A desirable microorganism has the capability of consuming nutrients to convert a fermentable sugar to ethanol. Desirable microorganisms include inoculants such as the yeast, *Saccharomyces cerevisiae*, which is used in the fermentation of glucose into ethanol and carbon dioxide. Other desirable microorganisms are used in other biorefinery processes. Desirable microorganisms are not typically present in carbohydrate feedstocks. When desirable microorganisms are present in a carbohydrate feedstock, the number of viable cells present is typically too low to compete favorably with the other microorganisms commonly also present in the feedstock.

A contaminant microorganism is a microorganism that competes with the inoculant for and consumes the fermentable sugar and nutrients. Contaminant microorganisms produce undesirable products and/or produce alcohol at a much lower rate than would be produced by the inoculant.

Contaminant microorganisms include bacteria, fungi, wild or contaminant yeasts, and other microorganisms capable of metabolizing components of a carbohydrate feedstock to sustain the viability of the microorganism. Contaminant microorganisms contaminate carbohydrate feedstocks, consume the feedstock as a food source in support of their growth, multiply, and thus deplete the feedstock.

Contaminant microorganisms such as contaminant yeasts are often found in both industrial and beverage ethanol production, and can cause severe episodes of contamination, resulting in reduced ethanol productivity in a fermentation process. These unwanted microorganisms may be introduced into the process through the fermentable sugar (feedstock), process water, air, operators, and numerous other sources.

Contaminant microorganisms, such as bacteria, including lactic acid bacteria (species of *Lactobacillus*) produce products such as acetic and lactic acids from glucose feedstocks, that not only consume the feedstock and thus prevent feedstock conversion to desired products, but also adversely affect desirable microorganisms in a biorefining process. For example, acetic and lactic acids adversely affect the rate at which *Saccharomyces cerevisiae* converts glucose to ethanol. Other contaminant bacteria include species of *Pediococcus, Enterococcus, Acetobacter, Gluconobacter*, and *Clostridium*.

A nutrient means an element which supports growth and/or survival of the inoculant yeast or other inoculant microorganism, for example a nutrient may be a source of carbon, nitrogen, oxygen, sulfur, phosphorus, magnesium, and a variety of trace elements such as metals. A carbon source can be an alcohol such as methanol, or a hydrocarbon such as octane. A carbon source may also be the fermentable sugar. A nitrogen source can be urea, ammonia, an ammonium salt or a nitrate. A salt such as magnesium sulfate can provide magnesium and sulfur. Phosphorus can be supplied as a sodium or potassium salt, while oxygen can be supplied by introducing air into the process. Other forms of gaseous oxygen can be used, such as pure oxygen or oxygen/nitrogen mixtures. Other elements can be added directly or may be naturally present in process components.

A peroxygen-releasing compound is a nitrogen-free peroxygen-releasing compound. A nitrogen-free peroxygen-releasing compound is defined herein as any nitrogen-free material capable of releasing hydrogen peroxide or other oxygen-containing radicals upon addition to an aqueous system. The peroxygen-releasing compound may be an alkali metal, alkaline earth metal or transition metal compound of a percarbonate, perborate or peroxide, or a mixture of two or more thereof, provided the compounds in the mixture are compatible. Preferably the peroxygen-releasing compound is selected from the group consisting of sodium percarbonate, sodium perborate, sodium peroxide, calcium peroxide, magnesium peroxide and zinc peroxide. More preferably, the peroxygen-releasing compound is sodium percarbonate or sodium perborate. The peroxygen-releasing compounds may be used in hydrate form, e.g., sodium carbonate peroxyhydrate and sodium perborate monohydrate. Peroxygen-releasing compounds dissolve in aqueous systems to produce peroxide. For example, sodium percarbonate produces sodium carbonate and hydrogen peroxide by the following reaction:

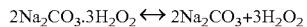

$$2Na_2CO_3.3H_2O_2 \leftrightarrow 2Na_2CO_3 + 3H_2O_2$$

The peroxygen-releasing compound may be in pure form or encapsulated to provide for enhanced stability when part of a formulation or for enhanced shelf life. The peroxygen-releasing compound may be supplied as a powder, pellet, pill, cake, or slurry. In addition, the peroxygen-releasing compound may be formulated with stabilizers, surfactants, additional nutrients, or additional sources of nitrogen for inoculant yeast. It will be appreciated by those skilled in the art that different formulations comprising peroxygen-releasing compounds may be preferred in different fermentation processes (e.g., depending on inoculant, fermentable sugar, availability of nutrients, among others). For example, a preferred formulation for use in molasses-based fermentation for the production of ethanol is a combination of a peroxygen-releasing compound and a vitamin B mixture, as molasses is known to contain less vitamin B than may be needed to sustain fermenting yeasts.

Preserve and preservation means treating a carbohydrate feedstock to prevent reaction or consumption of carbohydrate by contaminant microorganisms such as bacteria. Preservation provides a stable carbohydrate feedstock that does not undergo substantial change, such as would result from reaction or consumption of the carbohydrates due to microbial metabolism, over a period of time of at least one month. One measure of change is the microbial population of the preserved feedstock. When properly preserved, the carbohydrate feedstock does not undergo an increase in the microbial population in the feedstock of more than 1 $\log_{10}$ CFU/ml or 1 $\log_{10}$ CFU/g. Typically microbial population is expressed as $\log_{10}$ CFU/ml for liquid feedstocks and as $\log_{10}$ CFU/g for solid/semi-solid feedstocks. The expression $\log_{10}$ CFU/g can also be used for liquid feedstocks.

A second measure of change with respect to preservation is based on the concentrations of particular acids in the feedstock. Acids are known products resulting from reaction and/or consumption of carbohydrates by contaminant bacteria. For example, certain bacteria known to contaminate carbohydrate feedstocks produce lactic acid and acetic acid upon consumption of the carbohydrate. Increasing concentrations of lactic acid and acetic acid in a carbohydrate feedstock can be used to indicate whether the feedstock is properly preserved. When properly preserved, concentration of lactic acid in the carbohydrate feedstock is less than 0.60% (weight/volume) and concentration of acetic acid in the carbohydrate feedstock is less than 0.30% (weight/volume).

It will be further appreciated by those skilled in the art that other measures of change may be used. For example, detection of the presence of undesired compounds may indicate change, such as a product from metabolism of the carbohydrate feedstock. Detection methods may include spectrophotometry, chromatography, and other methods known to those skilled in the art. Still other measures may include physical changes to the carbohydrate feedstock such as specific gravity or viscosity.

Reactant means inoculant, fermentable sugar, optional nutrients as well as any other optional components in a fermentation broth. For purposes herein, reactant also includes process water.

Method for Growth Control

The method of this invention for controlling growth of one or more contaminant microorganisms comprises, consists essentially of or consists of adding a nitrogen-free peroxygen-releasing compound to one or more steps of a fermentation process.

The peroxygen-releasing compound may be added to any of the reactants such as the inoculant, fermentable sugar or process water prior to introducing the compound into the fermentation vessel.

The fermentation process may be batch or continuous. In a batch fermentation, preferably the peroxygen-releasing compound is added to the fermentation vessel prior to adding a fermentable sugar, more preferably prior to adding any of the reactants. In a continuous fermentation process, the peroxygen-releasing compound may be added in one or both of a yeast propagation step or in the contacting step to the fermentation vessel. If more than one fermentation vessel is used in series, preferably the peroxygen-releasing compound is added to the first or primary fermentation vessel in the series.

Preferably the peroxygen-releasing compound is added to the process prior to the production of significant amount of ethanol, or prior to the production of significant amounts of organic acid associated with growth of contaminant bacteria. By "significant amounts of ethanol", it is meant that the amount of ethanol in the fermentation broth is not more than 10% by weight, based on the total volume of the fermentation broth. By "significant amounts of organic acids", it is meant that the amount of organic acids in the fermentation broth is not more than 0.3% by weight, based on the total volume of the fermentation broth. Preferably the peroxygen-releasing compound is added early in the fermentation process, such as during the propagation of inoculant yeast, before, or just after inoculant yeast has been introduced into the fermentation vessel.

In another embodiment, the peroxygen-releasing compound is added to the fermentation process prior to the introduction of inoculant into the fermentation vessel. In this embodiment, the peroxygen-releasing compound may be added to the fermentable sugar or process water or both, prior to introducing either of these reactants to the fermentation vessel and the peroxygen-releasing compound/fermentable sugar and/or the peroxygen-releasing compound/process water is introduced to the fermentation vessel prior to introducing the inoculant to the fermentation vessel. For example the peroxygen-releasing compound may be added to one or more steps of providing the fermentable sugar, such as to one or more steps of a wet mill or dry grind process.

When the fermentation process includes a sugarcane- or sugar beet- or molasses-based fermentable sugar, it is typical to have fermentation vessels in series, having a first, second or even third or more fermentation vessel as a series of vessels where the fermentation broth is successively transferred into each fermentation vessel as part of the fermentation cycle. In this embodiment, the peroxygen-releasing compound is preferably added to the first fermentation vessel.

Alternatively, in a fermentation process where sugarcane or sugar beet or molasses is used as the fermentable sugar, the peroxygen-releasing compound is added to the fermentable sugar prior to contacting the fermentable sugar with inoculant. The peroxygen-releasing compound may be added during the storage of the fermentable sugar. Such step of adding the peroxygen-releasing compound during storage is contemplated herein as a step of the process for providing the fermentable sugar, prior to introducing the fermentable sugar into the fermentation vessel.

The peroxygen-releasing compound may also be added to an empty fermentation vessel, prior to adding the reactants.

In another alternative, for a batch process in which sugarcane or molasses is the fermentable sugar, and in which the inoculant is recycled at the completion of each fermentation cycle, the peroxygen-releasing compound may be added to a yeast treatment stage (yeast propagation) prior to the beginning of a subsequent batch in a fermentation process. That is, the peroxygen-releasing compound is added into the yeast recycle stream, which is commonly referred to as yeast cream.

In one embodiment, the peroxygen-releasing compound is added to the process water. Such a step of adding the peroxygen-releasing compound to process water is contemplated herein as a step of the process for providing the process water, prior to introducing process water into the fermentation vessel. Process water includes any water that is introduced into the fermentation process from either external sources or recycled from other parts of the fermentation process.

In a molasses-based fermentation process, process water includes water used to dilute incoming molasses prior to fermentation, water added as part of the yeast preparation process, or water recycled from preceding fermentation steps, including yeast recycle stream.

In a dry grind fermentation process, process water includes water added into the steep tank, slurry tank, yeast propagation, or fermentation vessels. The process water may also be a recycle stream in a dry grind batch fermentation process, wherein the recycle stream is a stream produced after fermentation is complete, and is commonly referred to as backset or process condensate. These stages of the dry grind fermentation process are well known to those skilled in the art. See, for example, R. J. Bothast and M. A. Schlicher, Applied Microbiology and Biotechnology as cited hereinabove.

The fermentation process may further comprise or alternatively comprise following the contacting step, adding a peroxygen-releasing compound to the product of the contacting step which product comprises ethanol, separating ethanol from the product. Alternatively, the fermentation process may further comprise, following the contacting step, separating the ethanol from the remaining product, wherein the remaining product is fed, for example, into a beer-well, or a thin stillage tank and adding the peroxygen-releasing compound to the beer-well or thin stillage tank.

The peroxygen-releasing compound is added to the fermentation process in an amount to provide an effective amount to control growth of one or more contaminant microorganisms. Typically the peroxygen-releasing compound is added in an amount to provide a concentration of 0.0001% to 5% by weight, based on the total weight of the fermentation broth. Preferably, the peroxygen-releasing compound is added to the fermentation process to provide a concentration of the peroxygen-releasing compound of 0.0005% to 1%, more preferably from 0.002 to 1% by weight, based on the total weight of the fermentation broth. Most preferably, the peroxygen-releasing compound is added to the fermentation process to provide a concentration of the peroxygen-releasing compound of 0.005 to 0.5% by weight, based on the total weight of the fermentation broth.

The peroxygen-releasing compound may be in liquid or solid form, preferably in solid form, more preferably as part of a formulation designed to give optimal fermentation performance.

Preservation Method

As an embodiment of the present invention for controlling growth of contaminant microorganisms in a fermentation process, a nitrogen-free peroxygen-releasing compound may be added as a step in providing the fermentable sugar. More particularly, as defined herein, the fermentation process comprises process steps to produce and store carbohydrate feedstock wherein the carbohydrate feedstock comprises a fermentable sugar or is used to prepare a fermentable sugar. Thus, the step of providing a fermentable sugar may comprise contacting a carbohydrate feedstock with a nitrogen-free peroxygen-releasing compound. Thus, the method of this invention is also useful to prevent degradation in storage of a carbohydrate feedstock.

The carbohydrate content of the feedstock is at least 1% and preferably 1 to 70%, by weight, based on the total feedstock weight. A peroxygen-releasing compound is added in an effective amount. Typically the peroxygen-releasing compound is added in an amount to provide 0.0001 to 5%, based on total weight of the feedstock. Preferably, the peroxygen-releasing compound is added in an amount to provide 0.001 to 1%, more preferably 0.01 to 0.1%, based on total weight of the feedstock.

In this method, a peroxygen-releasing compound is contacted with a carbohydrate feedstock in an effective amount to protect the carbohydrate from the growth of undesirable microorganisms and thus to prevent deterioration of the feedstock. Deterioration of the feedstock can be determined by the populations of contaminant microorganisms present, or the concentration of microbial metabolites, such as organic acids, that generally indicate unintended and undesirable microbial activity in the feedstock. Microorganisms are thus substantially prevented from proliferating in the stored or transported feedstock following the addition of the composition.

The present invention may be used to control contaminant microorganisms during storage and transport, preserving the carbohydrate feedstock.

Surprisingly, the carbohydrate feedstock treated according to this invention remains stable for at least one month. By "stable", it is meant herein the addition of a peroxygen-releasing compound preserves the carbohydrate feedstock, where "preserve" is defined hereinabove as preventing reaction of or consumption of carbohydrate by contaminant microorganisms. A stable carbohydrate feedstock does not undergo an increase in the microbial population in the feedstock of more than 1 $\log_{10}$ CFU/ml or 1 $\log_{10}$ CFU/g. CFU, an abbreviation for colony forming unit, is a measure of microbial population in the feedstock. CFU is used to determine the number of viable microbial cells in a sample per unit volume or per unit mass, or the degree of microbial contamination in samples. A second measure of change is pH of the preserved feedstock. The pH of a properly preserved feedstock should not change by more than 0.5 pH units. However, as previously stated, pH change may not be sufficient under all circumstances to monitor preservation of a carbohydrate feedstock.

The carbohydrate feedstock is defined hereinabove.

In the present invention, a peroxygen-releasing compound is used as a preservative for carbohydrate feedstocks to impede contaminant microorganism activity and subsequent deterioration of the carbohydrate feedstock as a step in providing a fermentable sugar. Contaminant microorganisms include bacteria as disclosed in WO 2007/149450 and contaminant yeast as disclosed in U.S. patent application Ser. No. 12/467,728, filed May 18, 2009. The compound inhibits growth of certain bacteria that cause undesired decomposition of carbohydrates such as simple sugars to deleterious acids and also selectively to reduce the activity of contaminant yeasts.

EXAMPLES

Example 1

In this example, the susceptibility of yeast and lactic acid bacteria to sodium percarbonate was determined in molasses. Molasses was prepared by diluting molasses (B&G Foods, Inc., Roseland, N.J.) 1 part to 3.1 parts water to mimic conditions used for ethanol production based on a molasses feedstock (common in Latin America and Asia). The diluted molasses was autoclaved at 121° C. for 15 minutes to sterilize prior to use in the experiment. Cultures of lactic acid bacteria (LAB) (*Lactobacillus plantarum*, *Lactobacillus brevis*, *Lactobacillus fermentum*, and *Lactobacillus paracasei*) were prepared by inoculating MRS broth (available from Difco Laboratories Inc., Sparks, Md.) and incubating overnight at 32° C. with agitation. The bacteria were selected because they had previously been isolated from contaminated ethanol fermentation processes. Cultures of each organism were combined to create a bacterial cocktail and diluted in molasses to give $1.0 \times 10^7$, $1.0 \times 10^6$, and $1.0 \times 10^5$ bacteria/ml, or commonly expressed as colony forming units per milliliter or CFU/ml). Sodium percarbonate (Alfa Aesar, Ward Hill, Mass.) was prepared as a 2% solution immediately prior to use. Percarbonate was added to tubes containing 25 ml of inoculated molasses to give concentrations of 0, 100, 250, 500 and 1000 ppm. Tubes were incubated at 32° C. with agitation. After approximately 2 hours, bacterial levels present in each tube were enumerated by plating decimal dilutions of molasses onto the surface of MRS agar plates (Difco Laboratories Inc., Sparks, Md.). Plates were incubated overnight at 32° C. Results are provided in Table 1.

As can be seen from Table 1, when the starting concentration of LAB is $1.0 \times 10^5$ CFU/ml, a dose of 500 ppm percarbonate results in approximately a 3-log reduction in the level of bacteria in just two hours. At initial concentration of $1.0 \times 10^6$ or $1.0 \times 10^7$ CFU/ml, a dose of 500 ppm percarbonate results in a 2-log reduction. However, at a dose of 1000 ppm, all of the tested levels of LAB were reduced to below the detectable limit (10 CFU/ml) of the assay.

In a second part of this Example 1, the yeasts strains Ethanol Red, FermPro S, and SuperStart (commonly used as fermenting yeasts in the ethanol industry) were cultured overnight in Yeast Peptone Dextrose broth (YPD, Difco Laboratories Inc., Sparks, Md.). Individual strains were then suspended in dilute molasses as above to give approximately $1 \times 10^6$ CFU/ml and treated with various concentration of percarbonate for two hours as described above. Results are provided in Table 2.

As can be seen from Table 2, all of the three yeast strains were far more resistant to treatment with sodium percarbonate that the lactic acid bacteria. Treatment of $1.0 \times 10^6$ CFU/ml of yeasts in molasses with 500 ppm percarbonate resulted in less than a 1-log reduction of both Ethanol Red and FermPro S, and approximately a 1-log reduction in the concentration of SuperStart. Treatments of the yeast strains Ethanol Red and FermPro S with 1000 ppm percarbonate resulted in approximately 1-log reductions compared to the >6 log reductions found in the test with LAB above.

Thus, adding of a peroxygen compound significantly reduces the presence of the lactic acid bacteria *Lactobacillus plantarum*, *Lactobacillus brevis*, *Lactobacillus fermentum*, and *Lactobacillus paracasei*.

TABLE 1

| LAB inoculum density CFU/ml | Percarbonate Concentration | | | | |
|---|---|---|---|---|---|
| | 0 ppm (Control) | 100 ppm | 250 ppm | 500 ppm | 1000 ppm |
| $1.0 \times 10^5$ LAB | $1.73 \times 10^5$ | $8.90 \times 10^4$ | $1.80 \times 10^3$ | $1.70 \times 10^2$ | <10 CFU/ml |
| $1.0 \times 10^6$ LAB | $1.47 \times 10^6$ | $8.50 \times 10^5$ | $1.55 \times 10^5$ | $1.17 \times 10^4$ | <10 CFU/ml |
| $1.0 \times 10^7$ LAB | $1.62 \times 10^7$ | $6.90 \times 10^6$ | $1.68 \times 10^6$ | $1.20 \times 10^5$ | <10 CFU/ml |

TABLE 2

| Yeast strain | Percarbonate Concentration | | | | |
|---|---|---|---|---|---|
| | 0 ppm (Control) | 100 ppm | 250 ppm | 500 ppm | 1000 ppm |
| Ethanol Red | $9.90 \times 10^6$ | $7.90 \times 10^6$ | $5.00 \times 10^6$ | $1.99 \times 10^6$ | $4.90 \times 10^5$ |
| FermPro S | $6.20 \times 10^6$ | $7.30 \times 10^6$ | $3.00 \times 10^6$ | $1.43 \times 10^6$ | $2.90 \times 10^5$ |
| SuperStart | $1.26 \times 10^6$ | $1.22 \times 10^6$ | $3.80 \times 10^5$ | $1.07 \times 10^5$ | $6.00 \times 10^3$ |

Example 2

In order for any bacterial control method to be practical for use in the production of fuel ethanol, it must be capable of inactivating bacteria at a wide range of pH levels. The pH of ethanol production varies widely based on both incoming feedstock and enzyme requirements. In this example, the use of sodium percarbonate to inactivate lactic acid bacteria was demonstrated at pH 4.2 and 5.4.

Molasses (B&G Foods, Inc., Roseland, N.J.) was diluted 1 to 3.1 with water and sterilized as in Example 1. The prepared molasses was then divided into two lots and pH-adjusted using sulfuric acid to approximately pH 4.2 and 5.4, respectively. Cultures of LAB were prepared as in Example 1 and inoculated into the molasses to give approximately $1 \times 10^6$ CFU/ml. Sodium percarbonate (Alfa Aesar, Ward Hill, Mass.) was added to give 250, 500, and 750 ppm. Titration using standard iodometric methods indicated that sodium percarbonate contained approximately 27.6% hydrogen peroxide by weight, based on the dry solid. Levels of LAB were enumerated by dilution and plating onto the surface of MRS agar followed by incubation at 32° C. LAB were enumerated at approximately 2 and 24 hours after the addition of sodium percarbonate. Results are provided in Table 3.

TABLE 3

| Sodium percarbonate concentration | ppm as $H_2O_2$ | CFU/ml LAB at hour indicated | | |
|---|---|---|---|---|
| | | 0 | 2 | 24 |
| Molasses at pH 4.2 | | | | |
| 0 ppm (Control) | 0 | $1.54 \times 10^6$ | $1.30 \times 10^6$ | $5.25 \times 10^6$ |
| 250 ppm | 69 | | $7.85 \times 10^5$ | $8.75 \times 10^4$ |
| 500 ppm | 138 | | $8.40 \times 10^5$ | $7.90 \times 10^6$ |
| 750 ppm | 207 | | $3.10 \times 10^5$ | $1.50 \times 10^3$ |
| Molasses at pH 5.4 | | | | |
| 0 ppm (Control) | 0 | $1.14 \times 10^6$ | $1.60 \times 10^6$ | $1.92 \times 10^7$ |
| 250 ppm | 69 | | $3.95 \times 10^5$ | $7.50 \times 10^1$ |
| 500 ppm | 138 | | $3.85 \times 10^4$ | $1.50 \times 10^1$ |
| 750 ppm | 207 | | $2.80 \times 10^4$ | <10 |

As can be seen from Table 3, addition of sodium percarbonate resulted in a decrease in the level of viable LAB at all percarbonate levels. Increasing the level of percarbonate resulted in increased inactivation of LAB. In the molasses sample at pH 4.2, the addition of sodium percarbonate at 250, 500, and 750 ppm resulted in approximately 1-log reductions in the amount of LAB at 2 hours. At the 24 hour sample time, 750 ppm of sodium percarbonate was able to reduce the number of LAB by more than 3-log units. In experiments using molasses adjusted to pH 5.4, at the 2-hour sample time, both 500 and 750 ppm of sodium percarbonate were capable of reducing the levels of LAB present in the molasses by approximately 2-log. At the 24-hour sample time, a dose of only 250 ppm sodium percarbonate was capable of producing an almost 6-log reduction in the level of LAB. At 750 ppm, the level of LAB remaining was below the detection limit of the assay.

Example 3

In this example, calcium peroxide ($CaO_2$) was used to illustrate inactivate LAB isolates present in fuel ethanol production. Titration using standard iodometric methods indicated that calcium peroxide contained approximately 35.1% hydrogen peroxide by weight, compared to 27.6% by weight for sodium percarbonate. In order to compare the efficacy of calcium peroxide with sodium percarbonate, the amount of calcium peroxide was adjusted so that the active dose (ppm as $H_2O_2$) was the same as in Example 2.

Molasses was prepared as above and adjusted to pH 4.2 and 5.4 using sulfuric acid. Cultures of lactic acid bacteria were prepared as indicated in Example 1 and inoculated into the molasses to give approximately 10E6 CFU/ml. Levels of bacteria were confirmed by plating serial dilutions of the inoculated molasses onto the surface of MRS agar plates as in Example 1. Calcium peroxide was added at the levels indicated. Bacterial levels were enumerated at 2 and 24 hours following addition as described above. Results are provided in Table 4.

TABLE 4

| Calcium peroxide concentration | ppm as $H_2O_2$ | CFU/ml LAB at hour indicated | | |
|---|---|---|---|---|
| | | 0 | 2 | 24 |
| Molasses at pH 4.2 | | | | |
| 0 ppm (Control) | 0 | $2.31 \times 10^6$ | $3.02 \times 10^6$ | $1.39 \times 10^7$ |
| 197 ppm | 69 | | $2.33 \times 10^6$ | $4.25 \times 10^6$ |
| 393 ppm | 138 | | $1.22 \times 10^6$ | $1.00 \times 10^1$ |
| 590 ppm | 207 | | $4.70 \times 10^5$ | <10 |
| Molasses at pH 5.4 | | | | |
| 0 ppm (Control) | 0 | $1.91 \times 10^6$ | $2.65 \times 10^6$ | $8.20 \times 10^6$ |
| 197 ppm | 69 | | $8.90 \times 10^5$ | $4.00 \times 10^4$ |
| 393 ppm | 138 | | $5.00 \times 10^2$ | <10 |
| 590 ppm | 207 | | $8.00 \times 10^4$ | <10 |

Similar to results for sodium percarbonate, calcium peroxide was able to significantly reduce the level of LAB in molasses at both pH levels. In molasses at pH 4.2, 197 and 393 ppm of calcium peroxide resulted in only slight reductions in LAB at the 2 hour sample time. The addition of 590 ppm of calcium peroxide was able to reduce the population of LAB by approximately 1 log. At 24 hours, the addition of 197 ppm calcium peroxide resulted in approximately 1 log reduction, whereas 393 and 590 ppm were able to reduce the population of LAB by more than 6-log units. In molasses at pH 5.4, 590 ppm of calcium peroxide was able to reduce the level of LAB from $2.65 \times 10^6$ to $8.0 \times 10^4$ CFU/ml at the 2 hour time point. At 24 hours, 393 ppm calcium peroxide reduced the levels of LAB to below the detection limit.

Example 4

Canadian patent application 2,300,807 describes the use of urea hydrogen peroxide (UHP) to prevent bacterial growth in fermentation processes. Similar to sodium percarbonate and calcium peroxide, UHP may serve as a peroxygen-releasing compound and inactivate bacterial contaminants of ethanol production. However, for any method to be practical in an industrial setting, the peroxygen-releasing compound must be stable for long periods of time during storage. Ambient temperatures in Asia and Latin America often reach 40° C. during the sugarcane (source of molasses used for ethanol production) growing season. In this example, various peroxygen-releasing compounds were tested for their stability during storage at 40° C.

A dry oven was used to store samples of the peroxygen-releasing compounds at 40° C. The oven was allowed to equilibrate overnight. Two-gram duplicate samples of each of the following peroxygen-releasing compounds were dispensed into aluminum weighing dishes: sodium percarbonate (Alfa Aesar, Ward Hill, Mass.), sodium percarbonate FB 400 (Solvay Chemicals, Inc., Houston, Tex.), sodium percarbonate FB 400C (Solvay Chemicals, Inc.), calcium peroxide (Sigma-Aldrich Co., St. Louis, Mo.), magnesium peroxide (Sigma-Aldrich Co.), and urea hydrogen peroxide (Sigma-Aldrich Co.). After six days, samples were analyzed for levels of hydrogen peroxide using standard iodometric titration. Results are provided in Table 5.

TABLE 5

| Peroxygen-Releasing Compound | Sample No. | % H$_2$O$_2$ Day 0 | % Remaining H$_2$O$_2$ Day 0 | % H$_2$O$_2$ Day 6 | % Remaining H$_2$O$_2$ Day 6 | % H$_2$O$_2$ Day 14 | % Remaining H$_2$O$_2$ Day 14 |
|---|---|---|---|---|---|---|---|
| Sodium percarbonate (Alfa Aesar) | 1 | 27.48 | 100 | 27.12 | 99 | 27.11 | 99 |
|  | 2 | 27.38 | 100 | 27.05 | 99 | 26.99 | 99 |
| Sodium percarbonate (FB 400) | 1 | 23.81 | 100 | 22.80 | 96 | 22.80 | 96 |
|  | 2 | 23.66 | 100 | 22.74 | 96 | 22.67 | 96 |
| Sodium percarbonate (FB 400C) | 1 | 26.34 | 100 | 25.37 | 96 | 25.35 | 96 |
|  | 2 | 26.25 | 100 | 25.45 | 97 | 25.27 | 96 |
| Calcium peroxide | 1 | 34.71 | 100 | 33.66 | 97 | 33.62 | 97 |
|  | 2 | 34.73 | 100 | 33.60 | 97 | 33.57 | 97 |
| Magnesium peroxide | 1 | 10.66 | 100 | 10.66 | 100 | 10.64 | 100 |
|  | 2 | 10.72 | 100 | 10.68 | 100 | 10.65 | 99 |
| Urea hydrogen peroxide | 1 | 34.53 | 100 | 0.24 | <1 | 0.08 | 0 |
|  | 2 | 34.56 | 100 | 0.25 | <1 | 0.08 | 0 |

As can be seen from Table 5, all three of the sodium percarbonate samples were stable during 6 and 14 days of storage at 40° C., with between 96 and 99% of the relative hydrogen peroxide retained at day 6 of storage. Calcium peroxide was also stable during storage, with 97% relative hydrogen peroxide being retained. Magnesium peroxide was the most stable of the peroxygen-releasing compounds tested with 100% of the relative hydrogen peroxide being retained after 6 days of storage at 40 C and 99-100% after 14 days of storage. In contrast, urea hydrogen peroxide was not stable during storage. Samples containing approximately 35% hydrogen peroxide at day 0 were reduced to below 1% hydrogen peroxide at day 6 of storage. This lack of storage stability would make urea hydrogen peroxide an impractical peroxygen-releasing compound for inactivation of bacterial contaminants during ethanol production.

Example 5

An additional benefit to the use of sodium percarbonate as a peroxygen-releasing compound is that it is capable of reducing contaminant bacterial populations in the presence of fermenting yeasts. In this experiment, UHP and sodium percarbonate were used to inactivate bacterial contaminants of ethanol production in dilute molasses at pH 5.0 in the presence of 10E6 CFU/ml yeast.

Cultures of lactic acid bacteria (LAB) were prepared as in Example 1 above. Molasses was diluted 1:3.1 with water as in previous examples. The fermenting yeast Ethanol Red was cultured as in example 1. Populations of lactic acid bacteria and yeasts were determined by dilution plating on MRS agar and YPD agar, respectively. Overnight cultures of LAB were mixed to prepare a bacterial cocktail and inoculated into molasses (diluted 1:3.1 with water) adjusted to pH 5.0 to give approximately 6.11 Log CFU/ml. Cultures of yeasts were added to each tube at a concentration of approximately 6.80 Log CFU/ml. UHP (Sigma-Aldrich Co.) and sodium percarbonate (Alfa Aesar, Ward Hill, Mass.) were added to each tube to give a final concentration equivalent to 500 ppm as H$_2$O$_2$ (UHP contains approximately 34.5% H$_2$O$_2$, while sodium percarbonate contains approximately 27.6% H$_2$O$_2$). The amount of UHP added was 1450 ppm. The amount of percarbonate added was 1812 ppm. Tubes were then incubated at 32° C. with agitation. The levels of LAB at 2 and 6 hours after inoculation were monitored by plating samples of the molasses on plates of MRS Agar containing 10 ppm amphotericin (Sigma-Aldrich Co.). Amphotericin inhibits the growth of yeast, facilitating enumeration of bacteria only. Results are provided in Table 6.

TABLE 6

| Sample | ppm as H$_2$O$_2$ | Log CFU/mL of LAB at hour indicated | | |
|---|---|---|---|---|
|  |  | 0 | 2 | 6 |
| Control | 0 | 6.11 | 6.35 | 6.40 |
| UHP | 500 |  | 3.36 | 1.85 |
| percarbonate | 500 |  | 1.95 | <1 |

As can be seen from Table 6, at equivalent concentrations of hydrogen peroxide, sodium percarbonate is able to reduce the population of LAB by almost 5 log units in 2 hours of incubation at 32° C. An equivalent concentration of UHP reduced the population of LAB by only 3 log units. At 6 hours of incubation, the levels of LAB present were reduced to below the detectable limit by sodium percarbonate, while bacteria were still detectable in molasses treated with UHP. These results demonstrate that sodium percarbonate is surprisingly more effective at controlling bacterial populations in ethanol fermentation processes where bacterial populations must be reduced in the presence of fermenting yeasts.

What is claimed is:

1. A method for controlling growth of contaminant microorganisms in a fermentation process comprising adding a nitrogen-free peroxygen-releasing compound to one or more steps of a fermentation process, wherein the fermentation process comprises (i) providing a fermentation vessel; (ii) providing an inoculant, a fermentable sugar and process water; (iii) introducing separately, or in any combination, the inoculant, fermentable sugar and process water into a fermentation vessel to provide a fermentation broth; and (iv) contacting the inoculant with the fermentable sugar in the fermentation vessel at a temperature at which the inoculant converts the fermentable sugar to ethanol.

2. The method of claim 1 further comprising adding nutrients to one or more of the inoculant, fermentable sugar and process water or directly to the fermentation vessel.

3. The method of claim 2 wherein the peroxygen-releasing compound is added to the inoculant, fermentable sugar or process water prior to introducing the inoculant, fermentable sugar or process water into the fermentation vessel.

4. The method of claim 1 wherein the inoculant is a yeast inoculum produced by contacting a yeast starter culture and a nutrient composition in a propagation tank.

5. The method of claim 4 wherein the fermentation process is a batch fermentation, and the peroxygen-releasing compound is added to the fermentation vessel prior to adding the fermentable sugar to the fermentation vessel.

6. The method of claim 4 wherein the fermentation process is a continuous fermentation process and the peroxygen-releasing compound is added in the yeast propagation step to produce the yeast inoculum or during the contacting step (iv).

7. The method of claim 2 wherein the fermentable sugar is derived from corn using a dry grind process.

8. The method of claim 2 wherein the fermentable sugar is derived from corn using a wet mill process.

9. The method of claim 2 wherein the fermentable sugar is sugarcane- or sugar beet- or molasses-based fermentable sugar.

10. The method of claim 2 wherein the peroxygen-releasing compound is an alkali metal, alkaline earth metal or transition metal compound of a percarbonate, perborate or peroxide, or a mixture of two or more thereof, provided the compounds in the mixture are compatible.

11. The method of claim 10 wherein the peroxygen-releasing compound is selected from the group consisting of sodium percarbonate, sodium perborate, sodium peroxide, calcium peroxide, magnesium peroxide and zinc peroxide.

12. The method of claim 11 wherein the peroxygen-releasing compound is sodium percarbonate or sodium perborate.

13. The method of claim 12 wherein the peroxygen-releasing compound is used in hydrate form.

14. The method of claim 1 wherein the peroxygen-releasing compound is added in an amount to provide a concentration of the peroxygen-releasing compound of 0.0001% to 5%, based on the total weight of the fermentation broth.

15. The method of claim 14 wherein the peroxygen-releasing compound is added in an amount to provide a concentration of the peroxygen-releasing compound of 0.0005% to 1%, based on the total weight of the fermentation broth.

16. The method of claim 14 wherein the peroxygen-releasing compound is added in an amount to provide a concentration of the peroxygen-releasing compound of 0.002% to 1%, based on the total weight of the fermentation broth.

17. The method of claim 1 further comprising following the contacting step, adding a peroxygen-releasing compound to the product of the contacting step.

18. The method of claim 1 wherein the step of providing the fermentable sugar comprises producing and storing a carbohydrate feedstock wherein the peroxygen-releasing compound is added to the carbohydrate feedstock and wherein the carbohydrate feedstock comprises a fermentable sugar and further wherein the carbohydrate content of the feedstock is at least 1% by weight, based on the total feedstock weight and the peroxygen-releasing compound is added in an amount to provide 0.0001 to 5% of the peroxygen-releasing compound, based on total weight of the feedstock.

19. The method of claim 18 wherein the carbohydrate content of the feedstock is 1 to 70% by weight, based on the total feedstock weight and the peroxygen-releasing compound is added in an amount to provide 0.001 to 1% of the peroxygen-releasing compound, based on total weight of the feedstock.

20. The method of claim 18 wherein the feedstock is a sugar-based feedstock.

21. The method of claim 18 wherein the feedstock is a cellulose feedstock.

22. A method according to claim 1 wherein the fermentation process further comprises after step (iv), adding the nitrogen-free peroxygen-releasing compound to the product of the contacting step which product comprises ethanol.

23. A method according to claim 1 wherein the fermentation process further comprises after step (iv), separating the ethanol from the product of the contacting step which product comprises ethanol to provide a remaining product, wherein the remaining product is fed, into a beer-well or a thin stillage tank and adding the a nitrogen-free peroxygen-releasing compound to the beer-well or thin stillage tank.

* * * * *